(12) United States Patent
Rollend et al.

(10) Patent No.: US 10,265,218 B2
(45) Date of Patent: Apr. 23, 2019

(54) OBJECT RECOGNITION AND PRESENTATION FOR THE VISUALLY IMPAIRED

(71) Applicant: The Johns Hopkins University, Baltimore, MD (US)

(72) Inventors: Derek M. Rollend, Baltimore, MD (US); Philippe M. Burlina, North Bethesda, MD (US); Kapil D. Katyal, Chevy Chase, MD (US); Kevin C. Wolfe, Lutherville, MD (US); Seth D. Billings, North Bethesda, MD (US); Cash J. Costello, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/671,696

(22) Filed: Aug. 8, 2017

(65) Prior Publication Data

US 2018/0036175 A1 Feb. 8, 2018

Related U.S. Application Data

(60) Provisional application No. 62/371,919, filed on Aug. 8, 2016.

(51) Int. Cl.
*G06K 9/00* (2006.01)
*A61F 9/08* (2006.01)
(Continued)

(52) U.S. Cl.
CPC ............ *A61F 9/08* (2013.01); *G06K 9/00671* (2013.01); *G06K 9/6202* (2013.01); *G06N 3/04* (2013.01); *G06N 3/0454* (2013.01)

(58) Field of Classification Search
CPC .......... B31D 5/0047; B31D 2205/0023; B31D 2205/0047; B31D 2205/0082;
(Continued)

(56) References Cited

U.S. PATENT DOCUMENTS

| 9,922,236 B2* | 3/2018 | Moore | G06K 9/00201 |
| 2011/0004271 A1* | 1/2011 | Dapper | A61N 1/025 607/53 |
| 2017/0278308 A1* | 9/2017 | Bleiweiss | G06T 19/20 |

OTHER PUBLICATIONS

P. Viola, et al., "Rapid Object Detection using a Boosted Cascade of Simple Features," Computer Vision and Pattern Recognition, 2001 (CVPR 2001), Proceedings of the 2001 IEEE Computer Society Conference, vol. 1. (2001), pp. I-511-I-518, 2001.
(Continued)

*Primary Examiner* — Tom Y Lu
(74) *Attorney, Agent, or Firm* — Todd R. Farnsworth

(57) ABSTRACT

Apparatuses, systems, and methods for object recognition and presentation are provided. An example apparatus may include a camera, an assistance feedback device, an input device, and processing circuitry. The processing circuitry may be configured receive an image from the camera, compare characteristic features within the image to an object identification dataset to identify object matches for a plurality of objects within the image, receive a selected name of an identified object from the user via the input device, and transmit assistance feedback to the user indicating a position of the selected object within the field of view via the assistance feedback device.

17 Claims, 7 Drawing Sheets

(51) Int. Cl.
*G06N 3/04* (2006.01)
*G06K 9/62* (2006.01)

(58) Field of Classification Search
CPC .............. C09D 119/003; C09D 163/00; G02B 2027/0138; G02B 2027/014; G02B 2027/0178; G02B 27/017; G06F 3/005; G06F 3/016; G06F 3/167; G06F 19/00; G06F 19/3418; G06F 3/011; G06K 9/002
See application file for complete search history.

(56) References Cited

OTHER PUBLICATIONS

Dr. Dobb's | The OpenCV Library | Nov. 1, 2000, Nov. 1, 2000 URL:http://www.drdobbs.com/open-source/the-opencv-library/184404319, last accessed on: Oct. 11, 2017.
Shengcai Liao, et al., "Learning Multi-scale Block Local Binary Patterns for Face Recognition," ICB 2007, LNCS 4642, pp. 828-837, Springer-Verlag Berlin Heidelberg 2007.
Kaiming He, et al., "Delving Deep into Rectifiers: Surpassing Human-Level Performance on ImageNet Classification," Microsoft Research, arXiv:1502.01852v1 (cs.CV), Feb. 6, 2015, 11 pages.
Olga Russakovsky, et al., "ImageNet Large Scale Visual Recognition Challenge," International Journal of Computer Vision (IJCV) 115 (2015) 211-252, 43 pages.
Ross Girshick, et al., "Rich feature hierarchies for accurate object detection and semantic segmentation," Tech report (v5), arXiv:1311.2524v5 (cs.CV), Oct. 22, 2014, 21 pages.
Shaoqing Ren, et al., "Faster R-CNN: Towards Real-Time Object Detection with Region Proposal Networks," arXiv:1506.01497v3 (cs.CV), Jan. 6, 2016, 14 pages.
Joseph Redmon, et al., "You Only Look Once: Unified, Real-Time Object Detection," arXiv:1506.02640v5 (cs.CV), May 9, 2016, 10 pages.
Wei Liu, et al., "SSD: Single Shot MultiBox Detector," arXiv:1512.02325v5 (cs.CV), Dec. 29, 2016, 17 pages.
Kai Kang, et al., "T-CNN: Tubelets with Convolutional Neural Networks for Object Detection from Videos," IEEE, arXiv:1604.02532v4 (cs.CV), Aug. 3, 2017, 11 pages.
Kai Kang, et al., "Object Detection from Video Tubelets with Convolutional Neural Networks," arXiv:1604.04053v1 (cs.CV), Apr. 14, 2016, 9 pages.
Tsung-Yi Lin, et al., "Microsoft COCO: Common Objects in Context," arXiv:1405.0312v3 (cs.CV) Feb. 21, 2015, 15 pages.
Alan W. Black, et al., "The Festival Speech Synthesis System," The Centre for Speech Technology Research, Informatics Forum, Human Communication Research Centre, University of Edinburgh, Scotland, UK (1997) Available at: http://www.cstr.ed.ac.uk/projects/festival, last accessed: Oct. 11, 2017.
Willie Walker, et al., "Sphinx-4: A Flexible Open Source Framework for Speech Recognition," Sun Microsystems, SMLI TR-2004-139, Nov. 2004, 15 pages.
Zdenek Kalal, et al., "Tracking-Learning-Detection," IEEE Transactions on Pattern Analysis and Machine Intelligence, vol. 34, No. 7, Jul. 2012, pp. 1409-1422.
Yangqing Jia, et al., "Caffe: Convolutional Architecture for Fast Feature Embedding," arXiv: 1408.5093v1 (cs.CV), Jun. 20, 2014, 4 pages.

\* cited by examiner

OBJECT RECOGNITION AND PRESENTATION FOR THE VISUALLY IMPAIRED

CROSS-REFERENCE TO RELATED APPLICATIONS

This application claims the benefit of U.S. Provisional Application No. 62/371,919 filed on Aug. 8, 2016, the entire contents of which are hereby incorporated herein by reference.

TECHNICAL FIELD

Example embodiments generally relate to visual imagery analysis and, more particularly, relate to apparatuses, systems, and methods for analyzing visual imagery data for presentation in usable formats for the visually impaired.

BACKGROUND

The ability for humans to visually sense features within the environment is a fundamental capability that enables effortless interaction with everyday objects. Too frequently, individuals find themselves with limited or severely impaired vision due to degenerative disorders, trauma, or other diseases. Such impairment can make mobility and interaction with objects an arduous task. While some solutions are available to assist the visually impaired in narrowly tailored ways, these solutions are often limited in applicability due to the fragmented nature of the solutions.

BRIEF SUMMARY OF SOME EXAMPLES

Various example embodiments of apparatuses, systems, and methods for object recognition and presentation for the visually impaired are provided herein. One example method may comprise capturing by a camera an image of a field of view of the camera, and comparing, by processing circuitry, characteristic features within the image to an object identification dataset to identify reference object image matches for a plurality of objects within the image. The plurality of objects identified in the image may be identified objects. The example method may further comprise determining, by the processing circuitry, a name for each identified object from the object identification dataset, determining, by the processing circuitry, locations of the identified objects within the field of view, and receiving, by an input device, a user request to communicate the identified objects within the field of view to the user. Further, the example method may comprise transmitting, by an output device, the name of each identified object in response to receiving the user request, receiving, by the input device, a selected name from the user, and determining, by the processing circuitry, a selected object based on the selected name. The selected object may be one of the identified objects. Additionally, the example method may comprise providing, by a visual prosthesis, assistance feedback to the user indicating a position of the selected object within the field of view.

An example system for object recognition and presentation is provided. In this regard, the example system may comprise a camera, an audio output device, an audio input device, a visual prosthesis, and processing circuitry. The processing circuitry may be configured to capture, via the camera, an image of a field of view of the camera, and compare characteristic features within the image to an object identification dataset to identify object matches for a plurality of objects within the image. The plurality of objects identified in the image may be identified objects. The processing circuitry may be further configured to determine a name for each identified object from the object identification dataset, determine locations of the identified objects within the field of view, and receive a user request, via the audio input device, to communicate the objects within in the field of view to the user. The processing circuitry may be further configured to transmit, via the audio output device, the name of each identified object in response to receiving the user request, receive, via the audio input device, a selected name from the user, and determine a selected object based on the selected name. The selected object may be one of the identified objects. The processing circuitry may be further configured to provide, via the visual prosthesis, assistance feedback to the user as a rendered modified image that indicates a position of the selected object within the field of view.

An example apparatus for object recognition and presentation is provided. The example apparatus may comprise a camera configured to capture an image of a field of view and to transmit that image. The camera may be in communication with processing circuitry. The example apparatus may further comprise an assistance feedback device in communication with the processing circuitry, and an input device in communication with the processing circuitry. The processing circuitry may be configured to receive the image from the camera, compare characteristic features within the image to an object identification dataset to identify object matches for a plurality of objects within the image. The plurality of objects identified in the image may be identified objects. The processing circuitry may be further configured to determine a name for each identified object from the object identification dataset, determine locations of the identified objects within the field of view, and receive a user request to communicate the identified objects within the field of view to a user via the input device. The processing circuitry may be further configured to transmit the name of each identified object in response to receiving the user request, receive a selected name from the user via the input device, and determine a selected object based on the selected name. The selected object may be one of the identified objects. The processing circuitry may be further configured to transmit assistance feedback to the user indicating a position of the selected object within the field of view via the assistance feedback device.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

FIG. 1 illustrates an example interaction between a user and an object recognition and presentation system according to an example embodiment;

FIG. 2 provides an example flowchart for object recognition and presentation according to an example embodiment;

DETAILED DESCRIPTION

Figure 1:
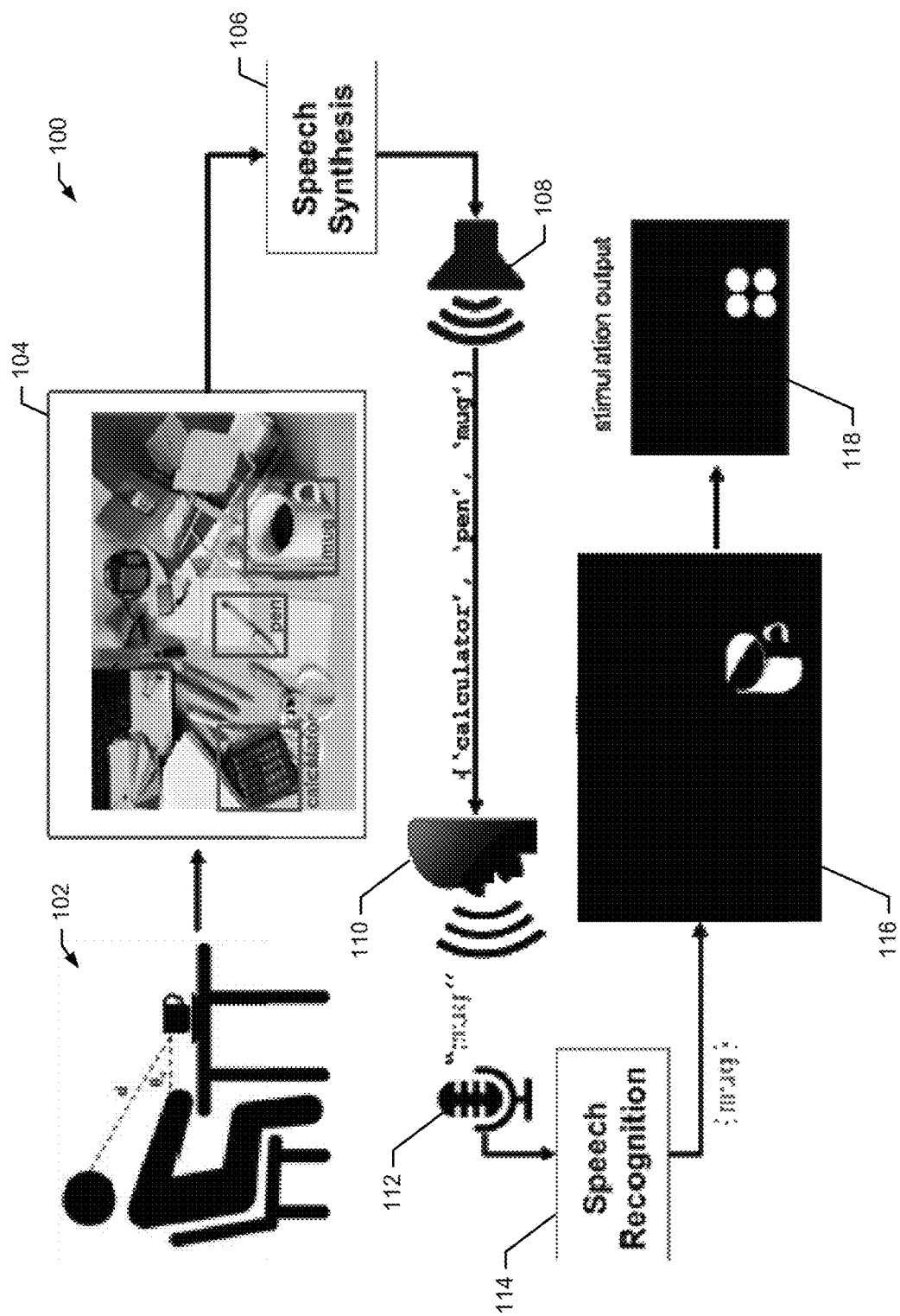

Some example embodiments now will be described more fully hereinafter with reference to the accompanying drawings, in which some, but not all example embodiments are shown. Indeed, the examples described and pictured herein should not be construed as being limiting as to the scope, applicability, or configuration of the present disclosure. Rather, these example embodiments are provided so that this disclosure will satisfy applicable legal requirements. Like reference numerals refer to like elements throughout.

As used herein the term "or" is used as the logical or where any one or more of the operands being true results in the statement being true. As used herein, the phrase "based on" as used in, for example, "A is based on B" indicates that B is a factor that determines A, but B is not necessarily the only factor that determines A.

U.S. application Ser. No. 15/206,453, filed Jul. 11, 2016, is hereby incorporated by reference in its entirety.

The advancement of medical device technology continues to provide new innovations that can assist individuals in overcoming medical limitations, such as the loss of sight. In the area of visual impairment, great strides have been made in the area of visual prostheses to provide sight or enhance an individual's ability to see. Such visual prostheses or implants can operate in a manner that essentially communicates directly with biological systems, such as the optic nerve, to provide visual information to the individual's brain for analysis and decision making.

By leveraging the abilities made available by a visual prosthesis and other vision enhancement medical devices, new forms of assistance can be provided to the visually impaired to assist in tasks such as object recognition and presentation to the individual to facilitate interaction between the visually impaired individual and the objects in their surroundings.

According to various example embodiments, a technique is provided herein to leverage image capture and assistance feedback systems to assist the visually impaired with interactions with the objects in their surroundings. In this regard, images captured by a camera, for example affixed to glasses or spectacles, can be analyzed to identify discrete objects within the images. The identities or names of the objects may be provided to the individual, for example, via audio feedback for selection by the user. Upon selection, for example, via a voice to text interface, a modified version of the captured images may be provided to the user, for example, via a visual prosthesis (e.g., retinal prosthesis, cortical implant, or the like), in a manner that filters or highlights the selected object to assist the user with locating and interacting with (e.g., picking up) the selected object.

FIG. 1 illustrates an example method 100 of interaction between a user and an object recognition and presentation system to improve a visually impaired individual's ability to interact with objects in their environment. To implement the example method 100, image capturing, audio output, audio input and feedback assistance devices may be involved. Further, processing circuitry for image analysis, speech synthesis, speech recognition, and presentation of feedback may also be utilized.

In the regard, the method 100 may begin with a scenario where a visually impaired individual may wish to locate and drink from a mug at 102. At 104, an image of objects on a table in front of the individual may be captured, for example by a camera affixed to the individual's glasses, and, since the scene is unknown, the captured image may be analyzed to identify at least some of the objects within the image. The scene captured in the image may be unknown. A variety of image analysis techniques can be used, according to various example embodiments, to identify the objects including algorithms that leverage machine learning and, for example, convolutional neural networks (CNNs) to identify the objects. In general, according to some example embodiments, a comparison of characteristic features within an image may be performed against an object identification dataset to identify object matches for a plurality of objects within the image. As shown at 104, for example, such a comparison has been performed and a calculator, a pen, and a mug have been identified.

Upon identifying objects within the captured image or images, the method 100 may continue by determining a name for each of the identified objects by leveraging, for example, nomenclature information associated or integrated with the object identification dataset. At 106, speech synthesis may be performed to prepare the determined names for output to the user as audible speech via an audible output device at 108. As shown, for example, the words "calculator," "pen," and "mug" may be spoken by the system.

At 110, the user may respond to the system with a verbal selection of an identified object. In this example scenario, the user may speak "mug" to make the selection. At 112, an audio input device may receive the user's speech selection of "mug" and perform a speech recognition analysis on the received speech at 114 to determine which identified object the user has selected.

Upon determining that the user has selected the mug, an image modification operation may be performed at 116 to filter or highlight the selected object in the captured image. According to some example embodiments, a portion of the image associated with or surrounding the selected object may be isolated or cropped and contrasted with the remainder of the image to highlight the selected object and more clearly reveal to the visually impaired user where, in the user's field of view, the selected object is located. In this regard, it can be seen at 116 that a portion of the image associated with the mug has been isolated and contrasted to more clearly present both the mug and its position in the field of view to the user. At 116, the modified image may be provided or displayed to the user for example, via communications with a visual prosthesis.

According to some example embodiments, a further modification to the captured image may be generated in the form of a stimulation output to a visual prosthesis at 118. In this regard, rather than or in addition to cropping and filtering (e.g., downsampling) the image with respect to the selected object, the image may be modified such that a visual representation of the position of the selected object within the field of view is provided. Such visual representation may be indicative of the data that may be transmitted to a visual prosthesis for stimulation. The visual representation may be shaped or colored in a manner that makes the representation readily discernable by an individual that is visually impaired.

With the position information provided as feedback to the user, the user may understand where in their surroundings an object of interest is located, based on the highlighted position of the object in the field of view. The user may then proceed to interact with the object, which, in this example scenario, may involve picking up the mug and taking a sip of coffee, for example.

Figure 2:
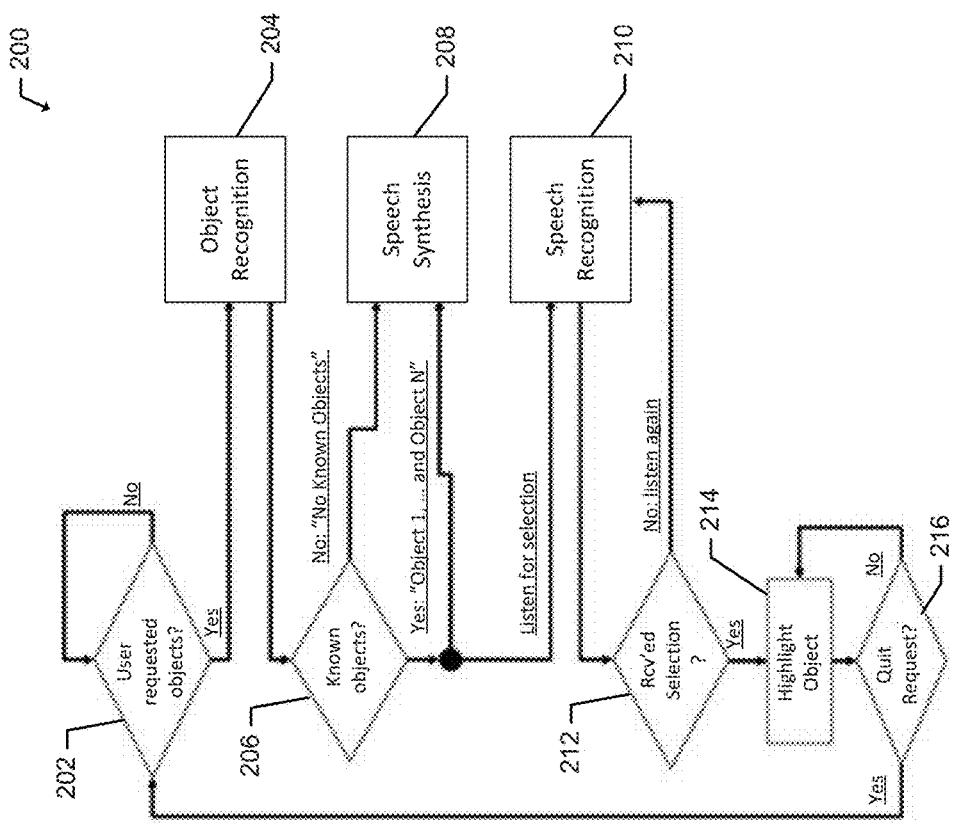

According to some example embodiments, FIG. 2 provides a detailed flow chart of another example method 200 for object recognition and presentation. In this regard, at 202, a user may make a request for an object in their field of view. In this regard, the request may be made in a variety of ways based on various example embodiments. For example, the user may speak a predefined phrase (e.g., "system, identify objects"), press a button, or the like that triggers a system to begin the method 200 by analyzing captured images from a camera (e.g., a two-dimension (2D) camera capturing a 2D image or a three-dimension (3D) camera capturing a 3D image) that is positioned in association with the user's field of view. According to some example embodiments, a four dimensional camera may be used, such as, a time of flight camera that captures four dimensional images including RGB (Red Green Blue) video with depth. If the system is not triggered, the method 200 may simply loop at 202 until a triggering request occurs. In one embodiment, and not shown at 202, image capturing may be repeatedly occurring at 202, such that one or more images have been captured when a triggering request 202 does occur. In another embodiment, and not shown at 202, in addition to image capturing, object recognition may also be occurring at 204, such that one or more images have been recognized when a triggering request 202 does occur.

If a request is made and the system is triggered, object recognition may be performed by the object recognition engine 204. As mentioned above, object recognition may involve comparing characteristic features within the image to an object identification dataset to identify object matches for a plurality of objects within the image. According to some example embodiments, objects to be identified and the reference objects may include faces of individuals. The object identification dataset may be a CNN. In the process of making the comparisons, a determination may be made at 206 if known objects have been identified in the image. In this regard, a confidence threshold may be set and only objects that are identified that meet or exceed the confidence threshold may be considered identified objects.

If no known objects are found, the system may provide feedback to the user that no known objects have been identified. A no known objects result may be output to the speech synthesis engine at 208 and the user may be verbally informed that no known objects have been identified in their field of view and the method may return to 202.

If known objects have been identified at 206, a bounding shape (e.g., box) may be defined around the object in the image. Further, if known objects are identified, then the names of the objects may be determined, for example, from the object identification dataset, and the speech synthesis engine 208 may be utilized to verbally output the names of the identified objects using text-to-speech. Upon outputting the names of the identified objects, the system may await a user selection at 212 of one of the identified objects by capturing audible information provided by the user. If a selection is not determined, then the system may continue to leverage the speech recognition engine 210 to determine a selection and may request additional information from the user.

Using the speech recognition engine 210, the system may determine the selected object from the user's speech and proceed to highlight the object in the image at 214 and provide the highlighted image to the user to assist the user with locating the object in the user's field of view. To highlight the image, a variety of image processing filters may be applied in order to enhance or increase the saliency of the selected object in the image while reducing the amount of visual information presented from the background. The bounding shape defined in association with the object recognition may be leveraged for the highlighting process. The type of processing filter used may be a function of a specific user efficacy or preference. According to some example embodiments, a modified variation of the image may be output to the user via a stimulation image that may be sent to a visual prosthesis. In this regard, the stimulation image may include a brighter shape or region in the area of the selected object in the image thereby assisting the user with locating the selected object in their physical surroundings. Upon completion of their interaction with the selected object, the user may quit or complete the request at 216 and return to 202.

To provide an improved user experience, according to some example embodiments, a sequence of images may be analyzed in view of the above, particularly since a user's field of view may be dynamically changing due to, for example, head movement. As such, an object tracking capability may be implemented that visually smooths image presentations to avoid "jumpy" object recognition locations being provided to the user during movement of the field of view and to stabilize the presentation to the user.

Since the comparison of image features to an object identification data set (i.e., object recognition), using for example a CNN, may evaluate still images instead of dynamic video scenes, object detection accuracy can decrease significantly when using video still captures from a moving camera. As a result, undesirable spurious detections (possibly in the form of false negatives) may occur that diminish performance and utility. As such, according to some example embodiments, object recognition may be performed at a slower interval relative to a video image capture speed (e.g., 30 frames per second). Further, the images used for object recognition may be filtered and movement may be accounted for using template matching techniques between object recognition events. For example, object identification may be performed on every n-th image (e.g., every third video image) after being subjected to filtering and image matching. A Kalman filter is one example of a temporal filter that focuses on stability and may be applied in this context. Other example filters that may be alternatively used in this regard include moving average filters and Gaussian temporal filters. The goal of the image filtering is to improve tracking of the objects over time, which is particularly relevant during times when object recognition fails to find a match. Thus, the application of the filter provides temporal stability of the objects detected.

Figure 3:
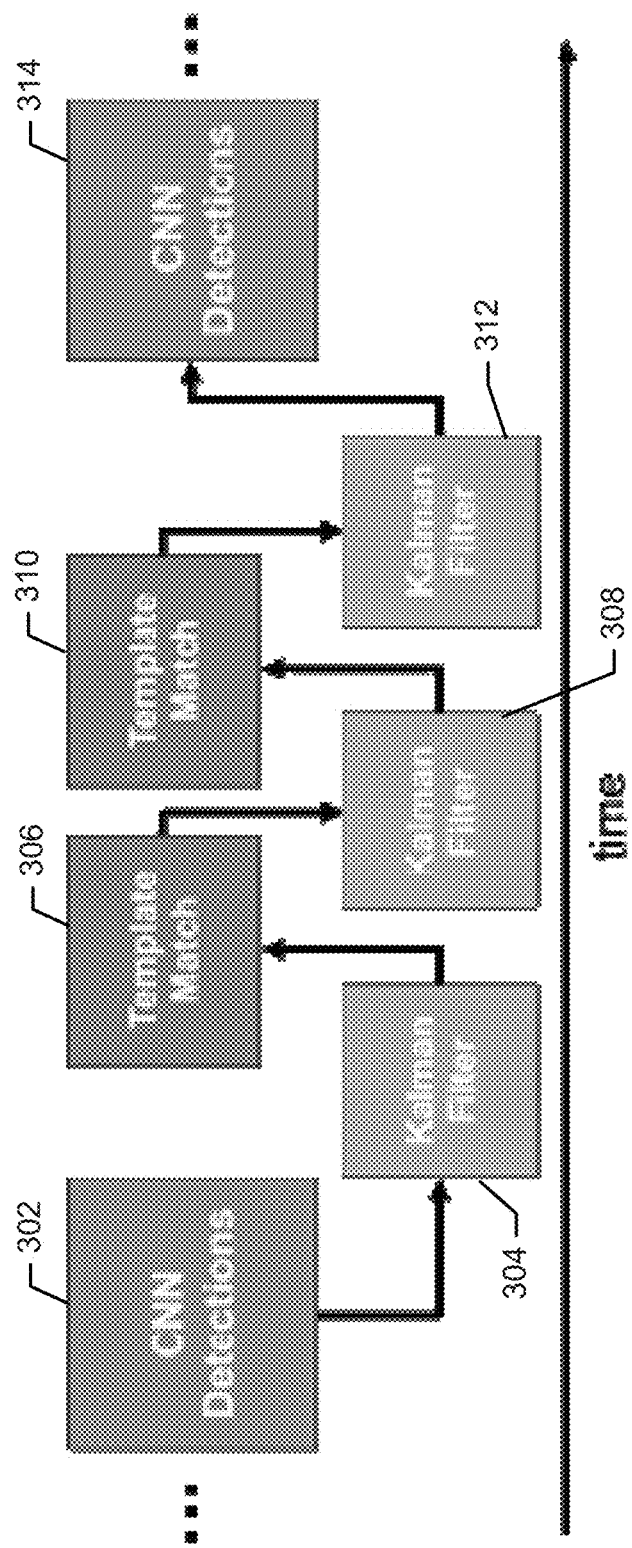
FIG. 3 illustrates example tracking according to an example embodiment.

In this regard, with reference to FIG. 3, a process of operations for object tracking and video image filtering is shown with respect to time. Although not shown in FIG. 3, it is understood that image capturing is being repeatedly performed (e.g., in a video mode) over time based on the user's field of view over time. In this regard, at 302, an object recognition in the form of, for example, a CNN detection may be performed to identify objects in a captured image. From this object recognition, a matching template may be defined that indicates the relative positions of objects or features within an image. The matching template may be used to track objects in between captured images or frames. The matching template may be derived from the most recent bounding box provided by the object recognition result. Once the matching template is derived, the matching template may be used to track the object even when object recognition fails to find the detected object. Subsequently, at 304, a filter (e.g., a Kalman filter) may be applied to a subsequent captured image and a template match may be performed at 306 on the subsequent image using the matching template to identify movement of the camera and associated movement of the objects within the field of view. Accordingly, for each image, which may be associated with time steps, a bounding shape (e.g., with a centroid width and height) may be adjusted. With the movement identified, the bounding shapes for the identified objects may be moved within the subsequent image in a corresponding manner and the result may be used for presentation to the user (i.e., without having performed object recognition on the subsequent image). In this regard, the movement may be represented by an estimated track state with, for example, four elements that describe the current xy position of the object and a next xy position of the object.

The filter (e.g., Kalman filter) may again be applied to a further subsequent image at 308, and yet another template match may be performed at 310 to relocate the identified objects and present the resultant modified image (e.g., in the form of a stimulation image) to the user. At 312, a filter may again be applied to a subsequent image in preparation for another object recognition at 314.

More specifically, with respect to tracking in view of the context provided above, according to some example embodiments, a Single Shot Multibox Detector (SSD) technique may be utilized. A Single Shot Multibox Detector (SSD) is one example of a high performing object recognition algorithm based on deep learning and convolutional neural networks. In this regard, when an object has been first detected by an SSD, a track for that object may be considered "soft" and initialized for the respective object since there is not yet an actual track. If the object is detected using SSD a minimum number of times (e.g., 5), then the track may be considered "hard" and the object may be added to a list of objects that continues to be included in the scene. A Kalman filter may be used at each timestep for the images in order to predict and measure the tracked object's bounding box centroid (x, y), width, and height. As such, the four elements of the estimated track state may be $[S_x, S_y, S_w,$ and $S_h]$ (e.g., x,y location and width and height of the tracked object). It is noted that more than one object may be tracked at a time.

To associate SSD-based detections with the tracked objects at each iteration, three criteria may be used, namely, matched class labels, minimum intersection over union (IOU), and a maximum Euclidean distance between centroids. The minimum IOU threshold, $T_{IOU}$, and the maximum distance threshold, $T_D$, may be determined empirically as follows. As mentioned above, an estimated track state may be defined by four elements that are related to an object's bounded box in x and y coordinates. In this regard, the four elements of the estimated track state may be $S_x, S_y, S_w,$ and $S_h$. As such, $T_{IOU}=0.1$ and $T_D=2*H_{track}$ where $H_{track}$ is the length of the hypotenuse formed by $S_w$ and $S_h$.

In the event that no track association is found for an SSD detection, a new track may be soft initialized. Conversely, if no matching SSD detection is found for an existing hard track, then basic template matching may be employed between the most recent SSD-detected bounding box for that track and an expanded search region centered at the current track centroid $(S_x, S_y)$. If the maximum normalized cross coefficient metric exceeds a defined threshold, $T_{TM}$, a match is declared and the image filter (e.g., Kalman) may be corrected with the measured location in the input frame. The stored bounding box for the given track may not be updated until a new associated SSD detection has been found. At each iteration, an age of each track may be incremented or increased for soft and hard tracks. The age of tracks may be reset if an SSD association has occurred or if a template has matched. Tracks that exceed a threshold age may be removed, thereby ensuring that any objects with false positives or objects that have exited the camera's field of view are no longer processed.

Based on the foregoing, according to some example embodiments, a 3D camera and 3D images may be utilized in object recognition and presentation as provided herein. However, the use of 3D may also allow some example embodiments to leverage the third, depth dimension of the image to further assist the visually impaired to interact with their surroundings. In this regard, the captured image or images may be filtered by depth, and areas of the scene with predetermined depth range from the user may be considered for object recognition. In this regard, a 2D image may be formed at the predefined depth for use in object recognition and presentation as provided herein.

With respect to tracking an object, according to some example embodiments, even if an object has been identified through object recognition, the object may need to appear in a minimum number of images, either through object recognition or through template tracking, to be considered an identified object for further interaction with respect to the user. As such, objects that only appear in a sequence of images for a relatively short period of time (number of images) need not be considered an option for interaction with by the user.

Further, depth information may be used to perform auditory cueing. A user may move their field of view to align with a selected object based on a determined centroid of a selected object in 3D (or 2D) and a spatial sound that uses, for example, a Head-Related Transfer Function (HRTF) to cue the user to the relative location of the selected object. According to some example embodiments, such auditory information could be conveyed, for example, via open-ear, bone-conducting headphones that do not interfere with the user's normal hearing. Such auditory cuing feedback may enable use by a broader visually impaired community outside of, for example, visual prosthesis users.

Figure 4:
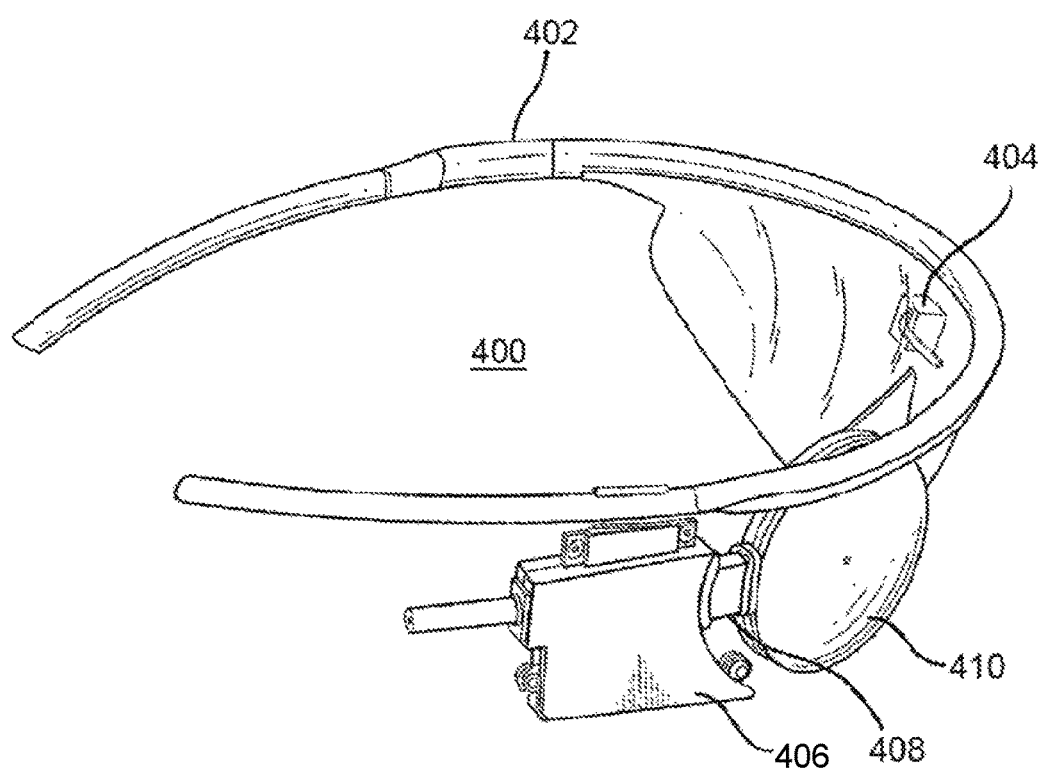
FIG. 4 shows a component for object recognition and presentation in the form of glasses with a camera according to an example embodiment.
Figure 5:
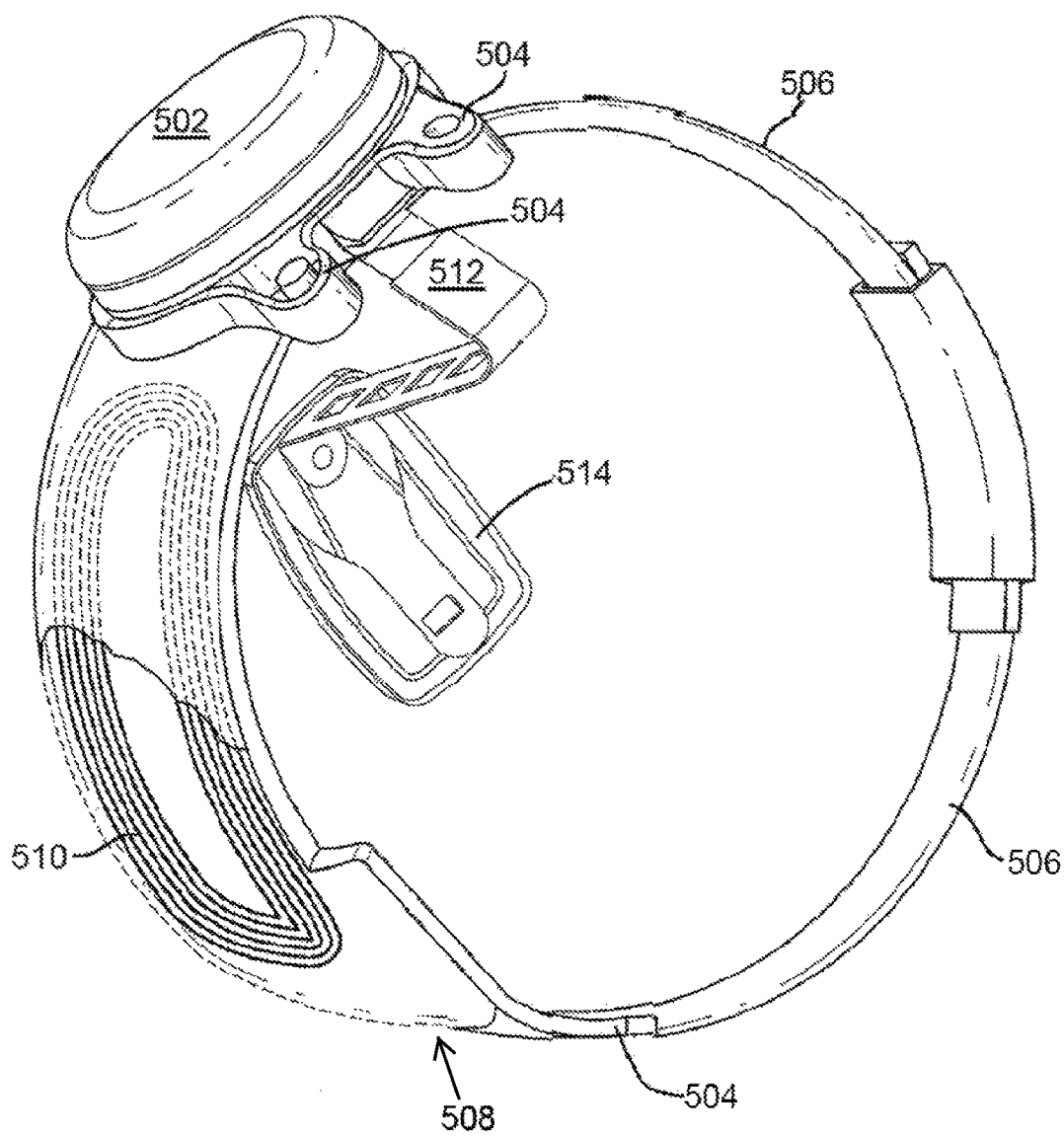
FIG. 5 shows a component for object recognition and presentation in the form of a retinal prosthesis according to an example embodiment.

FIGS. 4 and 5 show components of an example visual prosthesis in the form of a retinal prosthesis system that may be configured to perform object recognition and presentation in the form of the methods and techniques described herein. FIG. 4 shows glasses 400 that are worn external to the body and FIG. 5 shows a retinal prosthesis 500.

Referring to FIG. 4, the glasses 400 may include, for example, a frame 402 holding a camera 404, an external coil 410, an external coil support 408, and an electronics housing 406 operably coupled to the external coil 410 and the camera 404. The electronics housing 406 may also enclose the processing and radio frequency circuitry. Glasses 400 may also have audio output and input (e.g., one or more microphones, one or more speakers, bone-conduction headphones, etc.). In this configuration, the camera 404 may be configured to capture images including still or live video and generate a digital representation of the field of view of the camera 404. The digital representation may be sent to a processing unit (possibly housed in the electronics housing 406). The processing unit (which may be the same or similar to processing circuitry 602) may processes images as described herein. The processing unit, in accordance with various example embodiments, may process images, as described herein, and generate electrical stimulation patterns that may be communicated to the retinal prosthesis 500. In another embodiment, the processing unit may process images and provide image data to a display such as a heads-up display (HUD), head-mounted display (HMD), optical head-mounted display (OHMD), a see through HMD, etc. for augmented reality. With regard to the retinal prosthesis 500, the electrical stimulation data (that represent a stimulation image) may be sent via the external coil 410 and radio-frequency (RF) telemetry to an internal coil 510 of the retinal prosthesis 500. The internal coil 510 may receive the RF communicated information and transmit to a processor of the electronics package 502, which may be a microprocessor, an application specific integrated circuit (ASIC), or a field programmable gate array (FPGA). The processor of the electronics package 502 may in turn deliver stimulation to the retina of a subject via an electrode array 514. Array 514, according to some example embodiments, may be a 60-channel electrode array. The electrical stimulation patterns or data may be passed via electrodes of the array 514 that cause retinal cells to be stimulated. As described herein, the technique of stimulating the retinal cells to permit a user to visualize an image or information may be one technique of rendering the image or information for interpretation by the user.

With more specific reference to FIG. 5, a retinal prosthesis 500 is shown which may be implanted for interaction with the retina of a visually impaired individual. A flexible circuit associated with the implanted portion of the retinal prosthesis 500 may include the array 514 which is mounted by a retinal tack (not shown) or similar means to the epiretinal surface. The array 514 may be electrically coupled by a flexible circuit cable 512, which pierces the sclera, to electronics package 502, external to the sclera. The electronics package 502 may, include a processor, and be electrically coupled to an internal coil 510. The processor of the electronic package 502 may work together with the processing unit of the electronics housing 406 to implement various aspects of the example embodiments described herein. The internal coil 510 may receive power and data from an external coil 410, which is external to the body as described above. The electronics package 502 and internal coil 510 may be held together by a molded body 508. The molded body 508 may include suture tabs 504 for securing the retinal prosthesis 500 in the body. The molded body 508 may narrow to form a strap 506 which surrounds the sclera.

Figure 6:
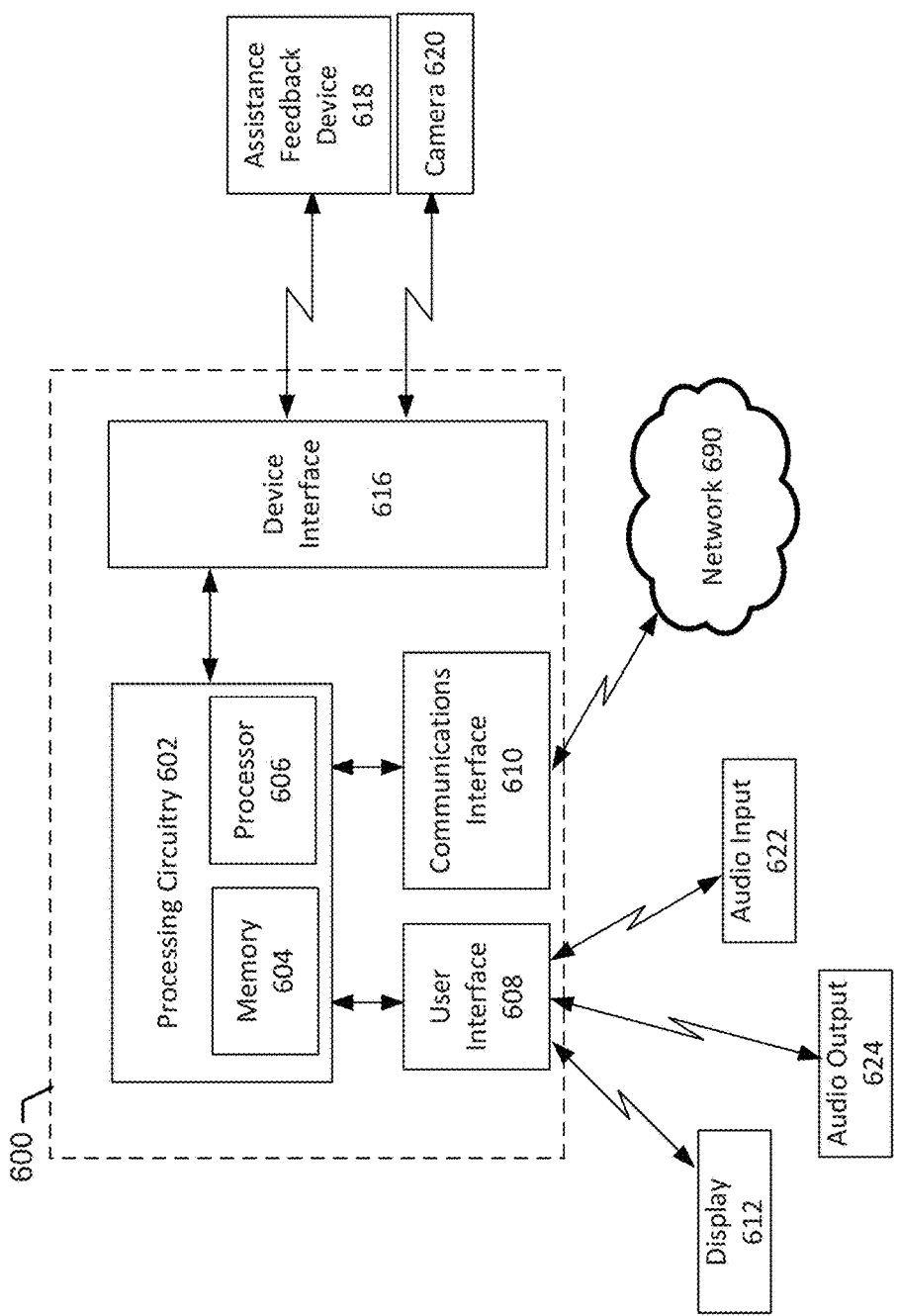
FIG. 6 shows an example apparatus for object recognition and presentation according to an example embodiment.

FIG. 6 provides a block diagram of an example of an apparatus 600 configured to perform object recognition and presentation according to some example embodiments. The glasses 400 and the retinal prosthesis 500 may together be one example of the apparatus 600.

Accordingly, FIG. 6 shows block diagrams of some internal components of an apparatus 600 that comprises processing circuitry 602 that may be in operative communication with or embody, a communications interface 610, a user interface 608, and a device interface 616. The processing circuitry 602 may interact with or embody a memory 604 and a processor 606. The processing circuitry 602 is configurable to perform operations described herein. In this regard, the processing circuitry 602 may be configured to perform computational processing and memory management according to an example embodiment. In some embodiments, the processing circuitry 602 may be embodied as a chip or chip set. In other words, the processing circuitry 602 may comprise one or more physical packages (e.g., chips) including materials, components or wires on a structural assembly (e.g., a baseboard). The processing circuitry 602 may be configured to receive inputs (e.g., via peripheral components such as under interface 608, communications interface 640, device interface 616, and including the memory 604), perform actions based on the inputs, and generate outputs (e.g., for provision to peripheral components). In an example embodiment, the processing circuitry 602 may include one or more instances of a processor 606, associated circuitry, and memory 604. As such, the processing circuitry 602 may be embodied as a circuit chip (e.g., an integrated circuit chip, such as a field programmable gate array (FPGA)) configured (e.g., with hardware, software or a combination of hardware and software) to perform operations described herein.

In an example embodiment, the memory 604 may include one or more non-transitory memory devices such as, for example, volatile or non-volatile memory that may be either fixed or removable. The memory 604 may be configured to store information, data, applications, instructions or the like for enabling, for example, object recognition and presentation and to carry out various functions in accordance with exemplary embodiments. For example, the memory 604 could be configured to buffer input data for processing by the processing circuitry 602. Additionally or alternatively, the memory 604 could be configured to store instructions for execution by the processing circuitry 602. Among the contents of the memory 604, applications may be stored for execution by the processing circuitry 602 in order to carry out the functionality associated with each respective application.

As mentioned above, the processing circuitry 602 may be embodied in a number of different ways. For example, the processing circuitry 602 may be embodied as various processing means such as one or more processors 606 that may be in the form of a microprocessor or other processing element, a coprocessor, a controller or various other computing or processing devices including integrated circuits such as, for example, an ASIC (application specific integrated circuit), an FPGA, or the like. In an example embodiment, the processing circuitry 602 may be configured to execute instructions stored in the memory 604 or otherwise accessible to the processing circuitry 602. As such, whether configured by hardware or by a combination of hardware and software, the processing circuitry 602 may represent an entity (e.g., physically embodied in circuitry—in the form of processing circuitry 602) capable of performing operations according to example embodiments while configured accordingly. Thus, for example, when the processing circuitry 602 is embodied as an ASIC, FPGA, or the like, the processing circuitry 602 may be specifically configured hardware for conducting the operations described herein. Alternatively, as another example, when the processing circuitry 602 is embodied as an executor of software instructions, the instructions may specifically configure the processing circuitry 602 to perform the operations described herein.

The communication interface 610 may include one or more interface mechanisms for enabling communication with other devices external to apparatus 600, via, for example, a network 690, such as a local area network. In some cases, the communication interface 610 may be any means such as a device or circuitry embodied in either hardware, or a combination of hardware and software that is configured to receive or transmit data from/to devices in communication with the processing circuitry 602. The communications interface 610 may be a wired or wireless interface and may support various communications protocols.

The user interface 608 may be controlled by the processing circuitry 602 to interact with a user. In this regard, via the user interface 608, the processing circuitry 602 may be configured to output to a user via an output device such as, for example, driving a display 612 and receive input from a user via an input device such as, for example, audio input 622, which may be, for example, a microphone. The user interface 608 may also produce outputs, for example, via audio output 624, which may be for example, a speaker. According to some example embodiments, the user interface may also operably couple to other user input devices such as, for example, a keyboard, mouse, touch screen, or the like.

The device interface 616 may be configured to interface with typically special purpose devices that are closely controlled (possibly via firmware) by the processing circuitry 602. In this regard, the device interface 616 may include a data bus that devices may be connected to for interaction with the processing circuitry 602. Via the device interface 616, the processing circuitry 602 may send control messages or output information to a device, and the processing circuitry 602 may receive circumstantial information from devices that may, at least in part, modify the operation of processing circuitry 602 based on the circumstantial information.

According to some example embodiments, the apparatus 600 may be operably coupled to an assistance feedback device 618. According to some example embodiments, the assistance feedback device 618 may comprise, for example, a visual prosthesis (e.g., retinal prosthesis 500) and a communications interface (e.g., coupled coils) to the visual prosthesis. According to some example embodiments, the assistance feedback device 618 may be a display (e.g., HUD, HMD, OHMD, etc.) that can provide visual feedback to a user that assists with interacting with their surroundings as provided herein. Further, according to some example embodiments, the assistance feedback device 618 may include a controllable inertial device or the like that can provide haptic feedback to a user. Further still, according to some example embodiments, the assistance feedback device 618 may include audio output that can provide feedback to the user. Additionally, in one embodiment, the assistance feedback device 618 may provide a combination of audio, visual, and haptic feedback to the user.

The device interface 616 may also operably couple to a camera 620 (e.g., camera 404). The camera 620 may be configured to capture an image of a field of view and transmit that image, for example, to the processing circuitry 602. The camera 620 may be configured to capture 2D or 3D images in a digital format and communicate the images to the processing circuitry 602 for analysis as provided herein. The camera 620 may be configured to capture four dimensional images with one of the dimension being depth (e.g., RGB-D).

In an example embodiment, the processing circuitry 602 may be embodied as, include or otherwise control, the apparatus 600 to perform object recognition and presentation as described herein. As such, in some embodiments, the processing circuitry 602 may be said to cause each of the operations described in connection with, for example, the methods 100 and 200, the method of FIG. 7, and the functionalities otherwise described herein. The processing circuitry 602 may therefore undertake the corresponding functionalities responsive to execution of instructions or algorithms configuring the processing circuitry 602 accordingly. The processing circuitry 602 may provide programmable control signals, selections, and the like to control the operation of the apparatus 600 responsive to execution of instructions stored in the memory 604.

As such, according to some example embodiments, the processing circuitry 602 may be configured to receive an image from the camera 620. The processing circuitry 602 may also be configured to compare characteristic features within the image to an object identification dataset (e.g., stored in the memory 604) to identify object matches for a plurality of objects within the image. The plurality of objects identified in the image may be referred to as identified objects. The processing circuitry 602 may also be configured to determine a name for each identified object from the object identification dataset, and determine locations of the identified objects within the field of view. The processing circuitry 602 may be configured to receive a user request via the user interface 608, or more specifically an input device operably coupled to the user interface 608, to communicate the identified objects within in the field of view to the user, and transmit, via the user interface 608, the name of each identified object in response to receiving the user request. Further, the processing circuitry 602 may be configured to receive a selected name from the user via, for example, an input device, and determine a selected object based on the selected name. The selected object may be one of the identified objects. The processing circuitry 602, via the assistance feedback device 618, may also transmit assistance feedback to the user indicating a position of the selected object within the field of view via the assistance feedback device 618.

According to some example embodiments, the processing circuitry 602 may also be configured to capture additional images within the field of view of camera 620, and repeatedly compare characteristic features within at least some of the additional images to the object identification dataset to identify object matches for the plurality of objects within the image. Further, the processing circuitry 602 may be configured to apply a filter, between iterations of comparing the characteristic features to the object identification dataset, to more than one additional captured image over time to estimate positions of the identified objects based on a prior location determination of the identified objects. The filter may be a Kalman filter applied to the more than one captured image. Further, the processing circuitry 602 may also be configured to perform at least one image template match iteration, between iterations of comparing the characteristic features to the object identification dataset, to more than one additional captured image over time to track movement of the objects in the more than one additional captured image.

According to some example embodiments, the processing circuitry 602 may be configured to cause the camera 620 to capture the image as a three-dimensional image. In this regards, according to some example embodiments, the processing circuitry 602 may be further configured to filter the image at a target depth. Additionally, the processing circuitry 602 may be configured to detect a depth of a target point within the image (e.g., a centroid of a selected object) and output a dynamically controlled audible output that is based on a depth of the selected object relative to a depth of the target point.

The processing circuitry 602 may also be configured to utilize a convolution neural network to compare the characteristic features within the image to an object identification dataset. According to some example embodiments, the processing circuitry 602 may receive, via the user interface 608, audible speech from the user and perform speech recognition to determine the name of the selected object. According to some example embodiments, the processing circuitry 602 may be configured to provide assistance feedback by rendering a modified version of the image (e.g., via the assistance feedback device 618) that contrasts the selected object or an area around the selected object with a remainder of the image. Further, according to some example embodiments, the processing circuitry 602 may be configured to render, via the assistance feedback device 618, a modified version of the image with an area around the selected object being cropped to define an object area and a background area. For example, the background area may be modified to create contrast with the selected object, by, for example, darkening, disabling, or nullifying the pixels of the background area. The processing circuitry 602 may be further configured to, according to some example embodiments, provide assistance feedback by rendering, via the assistance feedback device 618, a representation of the selected object. The processing circuitry 602 may be further configured to, according to some example embodiments, provide assistance feedback in the form of audible cueing, via an output device, to indicate a direction that the user should move to interface with the selected object. In this regard, the processing circuitry 602 may be configured to cue the user move, for example, their head to reposition the camera 620 to be centered at the selected object or move their hand in the captured image in a direction to engage the selected object. For example, the assistance feedback may be verbal cues from an output device indicated that the user should, for example, move their hand to the left. Additionally, the processing circuitry 602 may be configured to support visual cueing in the event that a selected object moves out of the field of view. In this regard, the processing circuitry 620 may be configured to analyze the captured images and determine a location of the selected object relative to a point (e.g., the center) of the field of view. The processing circuitry 620 may be configured to transmit assistance feedback in the form of a modified image that includes an indicator of where the user should move the field of view to bring the selected object back into the field of view. According to some example embodiments, the indicator may be a bright area at or near an edge of the modified image closest to a determined position of the selected object.

Figure 7:
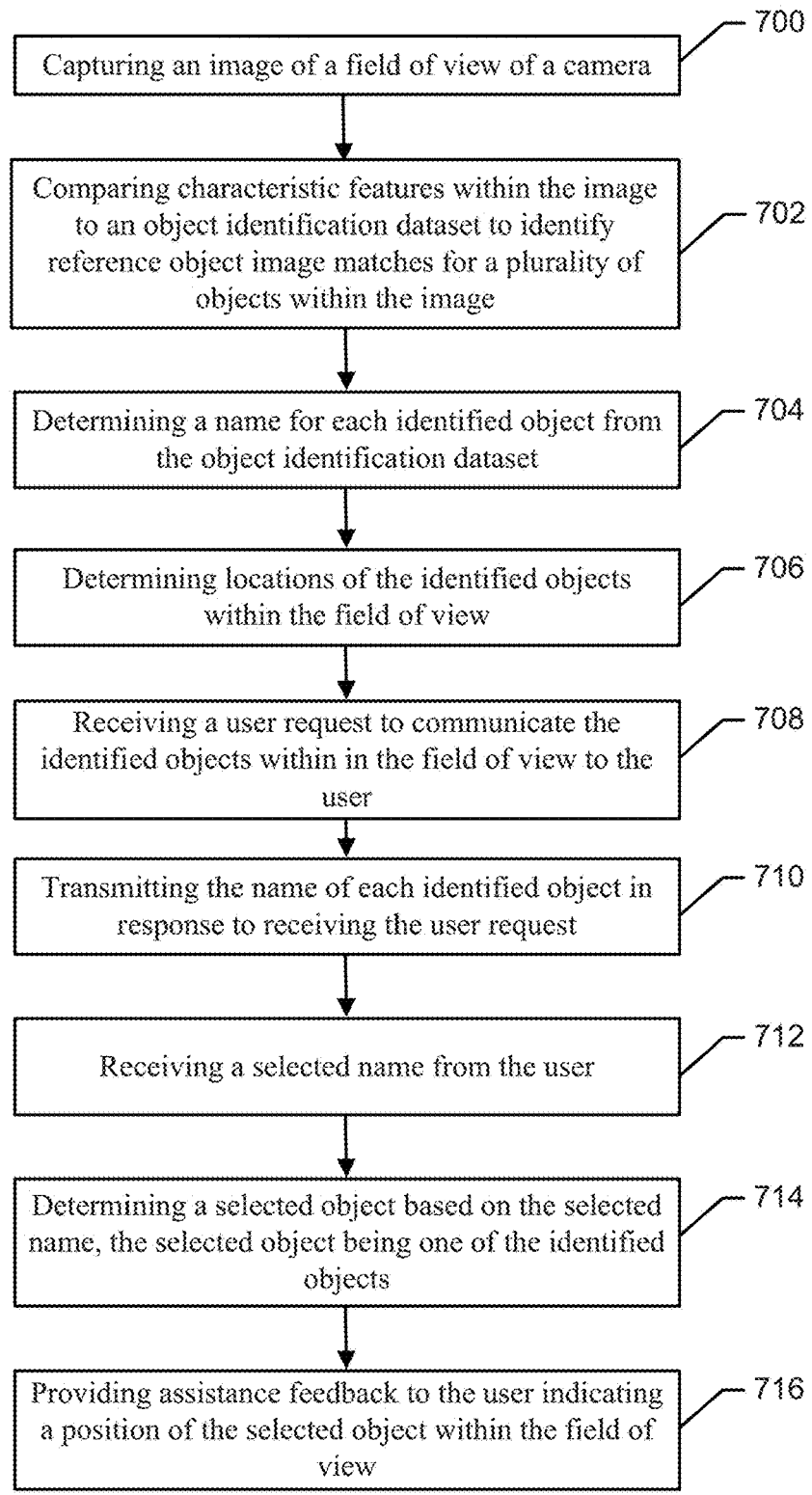
FIG. 7 shows an example flow chart for object recognition and presentation according to an example embodiment.

Referring now to FIG. 7, which is a block diagram of an example method for object recognition and presentation. The example method may be implemented by, for example, the apparatus 600. In this regard, the example method may include, at 700, capturing, by a camera, an image of a field of view of the camera (e.g., 404, 620), and, at 702 comparing, by processing circuitry, characteristic features within the image to an object identification dataset to identify object matches for a plurality of objects within the image. The plurality of objects identified in the image may be referred to as the identified objects. The example method may further include, at 704, determining, by the processing circuitry, a name for each identified object from the object identification dataset, and, at 706, determining, by the processing circuitry, locations of the identified objects within the field of view. Further, at 708, the example method may further comprise receiving, by an input device, a user request to communicate the identified objects within in the field of view to the user. At 710, the example method may further include transmitting, by an output device, the name of each identified object in response to receiving the user request, and, at 712, receiving, by an input device, a selected name from the user. The example method may further include, at 714, determining, by the processing circuitry, a selected object based on the selected name. In this regard, the selected object may be one of the identified objects. Additionally, at 716, the example method may include providing, for example by a visual prosthesis such as a retinal prosthesis, assistance feedback to the user indicating a position of the selected object within the field of view.

According to some example embodiments, the example method may further include capturing additional images within the field of view, and repeatedly comparing characteristic features within at least some of the additional images to the object identification dataset to identify object matches for the plurality of objects within the image. The example method may further include applying a filter, between iterations of comparing the characteristic features to the object identification dataset, to more than one additional captured image over time to estimate positions of the identified objects based on a prior location determination of the identified objects. The filter may be a Kalman filter that is applied to the more than one captured image.

According to some example embodiments, applying the filter may include performing at least one image template match iteration, between iterations of comparing the characteristic features to the object identification dataset, to more than one additional captured image over time to track movement of the objects in the more than one additional captured image. Further, according to some example embodiments, the example method may include capturing the image as a three-dimensional image or filter the image at a target depth. The example method may also include detecting a depth of a target point within the image and outputting a dynamically controlled audible output that is based on a depth of the selected object relative to a depth of the target point. Further, according for some example embodiments, the example method may include using a convolution neural network to compare the characteristic features within the image to an object identification dataset.

The example method may further include receiving the selected name of the object by receiving audible speech from the user and performing speech recognition to determine the name of the selected object. The example method may further comprise providing assistance feedback by rendering a modified version of the image that contrasts the selected object or an area around the selected object with a remainder of the image. According to some example embodiments, the example method may further comprise providing assistance feedback by rendering a modified version of the image with an area around the selected object being cropped to define an object area and a background area. In this regard, the background area may be modified to create contrast. Further, according to some example embodiments, the example method may also comprise providing assistance feedback by rendering a representation of the selected object.

As used herein, the term "module" is intended to include a computer-related entity, such as but not limited to hardware, software, or a combination of hardware and software. For example, a module may be, but is not limited to being a software or hardware implementation of a process, an object, an executable, and/or a thread of execution, which may be implemented via a processor or computer. By way of example, both an application running on a computing device and/or the computing device can be a module. One or more modules can reside within a process and/or thread of execution and a module may be localized on one computer and/or distributed between two or more computers. In addition, these modules can execute from various computer readable media having various data structures stored thereon. The modules may communicate by way of local and/or remote processes such as in accordance with a signal having one or more data packets, such as data from one module interacting with another module in a local system, distributed system, and/or across a network such as the Internet with other systems by way of the signal. Each respective module may perform one or more functions that will be described in greater detail herein. However, it should be appreciated that although such example is described in terms of separate modules corresponding to various functions performed, some examples need not necessarily utilize modular architectures for employment of the respective different functions. Thus, for example, code may be shared between different modules, or the processing circuitry itself may be configured to perform all of the functions described as being associated with the modules described herein. Furthermore, in the context of this disclosure, the term "module" should not be understood as a nonce word to identify any generic means for performing functionalities of the respective modules. Instead, the term "module" should be understood to be a modular entity that is specifically configured in, or can be operably coupled to, processing circuitry to modify the behavior and/or capability of the processing circuitry based on the hardware and/or software that is added to or otherwise operably coupled to the processing circuitry to configure the processing circuitry accordingly.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements or functions, it should be appreciated that different combinations of elements or functions may be provided by alternative embodiments without departing from the scope of the appended claims. In this regard, for example, different combinations of elements or functions than those explicitly described above are also contemplated as may be set forth in some of the appended claims. In cases where advantages, benefits or solutions to problems are described herein, it should be appreciated that such advantages, benefits or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. An apparatus configured to perform object recognition and presentation, the apparatus comprising:
    a camera configured to capture a plurality of images of a field of view and to transmit the plurality of images, the camera in communication with processing circuitry;
    an assistance feedback device in communication with the processing circuitry; and
    an input device in communication with the processing circuitry;
    the processing circuitry configured to:
        receive the plurality of images from the camera;
        compare characteristic features within a first image of the plurality of images to an object identification dataset to identify object matches for a plurality of objects within the first image;
        repeatedly compare characteristic features within additional images of the plurality of images to the object identification dataset to identify object matches;
        determine identified objects based on object matches in both the first image and the additional images;
        determine a name for each identified object from the object identification dataset;
        determine locations of the identified objects within the field of view;
        apply a filter, between iterations of comparing the characteristic features to the object identification dataset, to consecutive images over time to estimate positions of the identified objects based on a prior location determination of the identified objects to represent movement with an estimated track state prior to performing object recognition;
        receive a user request to communicate the identified objects within the field of view to a user via the input device;
        transmit the name of each identified object in response to receiving the user request;
        receive a selected name from the user via the input device;
        determine a selected object based on the selected name, the selected object being one of the identified objects; and
        transmit assistance feedback to the user indicating a position of the selected object within the field of view based on determined location and the estimated track state via the assistance feedback device.

2. The apparatus of claim 1, wherein the processing circuitry configured to apply the filter includes being configured to apply a Kalman filter to the consecutive images.

3. The apparatus of claim 2, wherein the processing circuitry configured to apply the filter includes being configured to perform at least one image template match iteration, between iterations of comparing the characteristic features to the object identification dataset, to more than one additional image over time to track movement of the objects in the more than one additional image.

4. The apparatus of claim 1, wherein the processing circuitry configured to capture the plurality of images is configured to capture the plurality of images as four-dimensional images including depth.

5. The apparatus of claim 4, wherein the processing circuitry is further configured to filter the plurality of images at a target depth.

6. The apparatus of claim 4, wherein the processing circuitry is further configured to detect a depth of a target point within the plurality of images and output a dynamically controlled audible output that is based on a depth of the selected object relative to a depth of the target point.

7. The apparatus of claim 1, wherein the processing circuitry is further configured to utilize a convolution neural network to compare the characteristic features within the plurality of images to an object identification dataset.

8. The apparatus of claim 1, wherein the processing circuitry configured to receive the selected name of the object includes being configured to receive audible speech from the user and perform speech recognition to determine the name of the selected object.

9. The apparatus of claim 1, wherein the processing circuitry configured to provide assistance feedback includes being configured to render a modified version of the image that contrasts the selected object or an area around the selected object with a remainder of the image.

10. The apparatus of claim 1, wherein the processing circuitry configured to provide assistance feedback includes being configured to render a modified version of the image with an area around the selected object being cropped to define an object area and a background area, and wherein the background area modified to create contrast with the selected object.

11. The apparatus of claim 1, wherein the processing circuitry configured to provide assistance feedback includes being configured to render a representation of the selected object.

12. The apparatus of claim 1, further comprising glasses, wherein the camera is affixed to the glasses, and wherein the processing circuitry is operably coupled to the glasses.

13. The apparatus of claim 1, wherein the processing circuitry is operably coupled to a visual prosthesis configured to output the assistance feedback, the visual prosthesis comprising an electrode array.

14. A system comprising:
a camera;
an audio output device;
an audio input device;
a visual prosthesis; and
processing circuitry, the processing circuitry configured to:
  capture, via the camera, a plurality of images of a field of view of the camera;
  compare characteristic features within a first image of the plurality of images to an object identification dataset to identify object matches for a plurality of objects within the first image;
  repeatedly compare characteristic features within additional images of the plurality of images to the object identification dataset to identify object matches;
  determine identified objects based on object matches in both the first image and the additional images;
  determine a name for each identified object from the object identification dataset;
  determine locations of the identified objects within the field of view;
  apply a filter, between iterations of comparing the characteristic features to the object identification dataset, to consecutive images over time to estimate positions of the identified objects based on a prior location determination of the identified objects to represent movement with an estimated track state prior to performing object recognition;
  receive a user request, via the audio input device, to communicate the objects within in the field of view to the user;
  transmit, via the audio output device, the name of each identified object in response to receiving the user request;
  receive, via the audio input device, a selected name from the user;
  determine a selected object based on the selected name, the selected object being one of the identified objects; and
  provide, via the visual prosthesis, assistance feedback to the user as a rendered modified image that indicates a position of the selected object within the field of view based on determined location and the estimated track state.

15. The system of claim 14, wherein the processing circuitry configured to apply the filter includes being configured to apply a Kalman filter to the consecutive images.

16. The system of claim 15, wherein the processing circuitry configured to apply the filter includes being configured to perform at least one image template match iteration, between iterations of comparing the characteristic features to the object identification dataset, to more than one additional image over time to track movement of the objects in the more than one additional image.

17. A method comprising:
capturing, by a camera, a plurality of images of a field of view of the camera;
comparing, by processing circuitry, characteristic features within a first image of the plurality of images to an object identification dataset to identify object matches for a plurality of objects within the first image;
repeatedly comparing characteristic features within additional images of the plurality of images to the object identification dataset to identify object matches;
determining identified objects based on object matches in both the first image and the additional images;
determining, by the processing circuitry, a name for each identified object from the object identification dataset;
determining, by the processing circuitry, locations of the identified objects within the field of view;
filtering, between iterations of comparing the characteristic features to the object identification dataset, to consecutive images over time to estimate positions of the identified objects based on a prior location determination of the identified objects to represent movement with an estimated track state prior to performing object recognition;
receiving, by an input device, a user request to communicate the identified objects within the field of view to the user;
transmitting, by an output device, the name of each identified object in response to receiving the user request;
receiving, by the input device, a selected name from the user;
determining, by the processing circuitry, a selected object based on the selected name, the selected object being one of the identified objects; and
providing, by a visual prosthesis, assistance feedback to the user indicating a position of the selected object within the field of view based on determined location and the estimated track state.

\* \* \* \* \*